(12) United States Patent
Malarme et al.

(10) Patent No.: US 8,058,049 B2
(45) Date of Patent: Nov. 15, 2011

(54) PROCESS FOR PRODUCING POXVIRUSES AND POXVIRUS COMPOSITIONS

(75) Inventors: Daniel Malarme, Oberhaslach (FR); Yves Cordier, Strasbourg (FR); Claude Sene, Strasbourg (FR)

(73) Assignee: Transgene S.A. (FR)

( * ) Notice: Subject to any disclaimer, the term of this patent is extended or adjusted under 35 U.S.C. 154(b) by 0 days.

(21) Appl. No.: 12/304,353

(22) PCT Filed: Jun. 15, 2007

(86) PCT No.: PCT/EP2007/005302
§ 371 (c)(1),
(2), (4) Date: May 18, 2009

(87) PCT Pub. No.: WO2007/147528
PCT Pub. Date: Dec. 27, 2007

(65) Prior Publication Data
US 2010/0008953 A1    Jan. 14, 2010

Related U.S. Application Data

(60) Provisional application No. 60/861,452, filed on Nov. 29, 2006.

(30) Foreign Application Priority Data

Jun. 20, 2006 (EP) ..................................... 06360027

(51) Int. Cl.
*C12N 7/02* (2006.01)
(52) U.S. Cl. ..................................... 435/239; 435/235.1
(58) Field of Classification Search .................. None
See application file for complete search history.

(56) References Cited

U.S. PATENT DOCUMENTS

| 7,118,754 B1 | 10/2006 | Balloul et al. |
| 2005/0208074 A1 | 9/2005 | Balloul et al. |
| 2006/0094104 A1 | 5/2006 | Grillberger et al. |
| 2006/0233834 A1 | 10/2006 | Guehenneux et al. |
| 2008/0318301 A1 * | 12/2008 | Lau ................................ 435/239 |

FOREIGN PATENT DOCUMENTS

| WO | WO 98/04705 A | 2/1998 |
| WO | WO 2004/022729 A1 | 3/2004 |
| WO | WO 2005/007840 | 1/2005 |
| WO | WO 2006/045438 | 5/2006 |

OTHER PUBLICATIONS

Katz et al (Journal of Virology 71:3178-3187, 1997).*
Katz et al (AIDS Research and Human Retroviruses 13:1497-1500, 1997).*
Gilbert et al (Cytotechnology 48:79-88, 2005).*
VP-SFM brochure. GIBCO Invitrogen Corporation, Carlsbad, CA. © 2002.*
Katz et al (Journal of Virology 71:3178-3187, 1997) (in IDS).*
Kwak et al (Virology 322:337-348, 2004).*
Meiser et al (Journal of General Virology 84:1383-1392, 2003).*
Spehner et al (Virology 273:9-15, 2000).*
Boulanger et al (Journal of General Virology 81: 675-687, 2000).*
Vanderplasschen et al (Journal of Virology 71:4032-4041, 1997).*
Katz, Ehud et al., "The Cytoplasmic and Transmembrane Domains of the Vaccinia Virus B5R Protein Target a Chimeric Human Immunodeficiency Virus Type 1 Glycoprotein to the Outer Envelope of Nascent Vaccinia Virions", Journal of Virology, 1997, pp. 3178-3187, vol. 71, No. 4.
Galmiche, Marie C. et al., "Expression of a functional single chain antibody on the surface of extracellular enveloped vaccinia virus as a step towards selective tumour cell targeting", Journal of General Virology, Society for General Microbiology, Spencers Wood, GB, Nov. 1997, pp. 3019-3027, vol. 78, No. 11.
Sutter, Gerd et al, "Nonreplicating vaccinia vector efficiently expresses recombinant genes", Proceedings of the National Academy of Sciences of USA, National Academy of Science, Washington, DC, Nov. 1992, pp. 10847-10851, vol. 89.
Smith, Geoffrey L. et al., "The formation and function of extracellular enveloped vaccinia virus", Journal of General Virology, Dec. 2002, pp. 2915-2931, vol. 83, No. 12.
Mcintosh, Alison A. G. et al, "Vaccinia Virus Glycoprotein A34R is Required for Infectivity of Extracellular Enveloped Virus", Journal of Virology, The American Society for Microbiology, Jan. 1996, pp. 272-281, vol. 70, No. 1.
Transgene, "Transgene Announces Positive Phase II Results for its HPV Therapeutic Vaccine in Precancerous Cervical Lesions", Internet Citation URL:http://www.transgene.fr/us/pdf/communique_presse/communiques_divers_2006/CP-US%20Eurogin%2025-04-06.pdf>, retrieved on Oct. 8, 2007.
Transgene (Squiban P), "Transgene's Therapeutic Vaccine MVA-MUC1-IL2 at ASCO", Internet Citation URL:http://vvvvw.transgene.com/us/pdf/communique_presse/communiques_divers_2005/PR-US_17-05-2005_ASCO_ POUMON.pdf>, retrieved on Oct. 8, 2007.
Trevor, Katrina T. et al., "Transduction of human dendritic cells with a recombinant modified vaccinia Ankara virus encoding MUC1 and IL-2", Cancer Immunology and Immunotherapy, Berlin, DE, Aug. 22, 2001, pp. 397-407, vol. 50, No. 8.
Written Opinion of the International Searching Authority dated Nov. 5, 2007.
International Preliminary Report on Patentability Jun. 16, 2008.
International Search Report dated Nov. 5, 2007.
Werden, Steven J. Of al., "*Poxvirus Host Range Genes*," 71 Advances in Virus Research 135-171 (Jan. 1, 2008).
European Office Action for corresponding European Patent Application No. 07 764 674.3-2405 mailed Aug. 10, 2010.

* cited by examiner

*Primary Examiner* — Mary E Mosher
(74) *Attorney, Agent, or Firm* — Buchanan Ingersoll & Rooney PC

(57) ABSTRACT

The present invention relates to compositions and pharmaceutical compositions comprising poxviruses and more particularly extracellular enveloped viruses. The present invention also relates to a process for producing poxviruses and poxviruses obtained thereof. Moreover, the present invention also relates to the use of said poxvirus and said composition for the preparation of a medicament.

6 Claims, 3 Drawing Sheets

Figure 1

Survival rate

| Groupe | VIRUS | DOSES pfu / souris | days after tumoral challenge | | | | | | | | | | |
|---|---|---|---|---|---|---|---|---|---|---|---|---|---|
| | | | 9 | 13 | 20 | 27 | 34 | 41 | 49 | 56 | 63 | 70 | 77 |
| 1 | IMV/EEV | 5,0 E+05 pfu | 100 | 100 | 100 | 100 | 100 | 100 | 90 | 65 | 60 | 60 | 60 |
| 2 | IMV | 5,0E+05 pfu | 100 | 100 | 100 | 100 | 95 | 95 | 60 | 40 | 35 | 30 | 20 |
| 3 | N33 | 5,0 E+05 pfu | 100 | 100 | 100 | 100 | 100 | 90 | 70 | 25 | 10 | 5 | 5 |

Figure 2

Pourcentage of tumor free Mices

| VIRUS | DOSES pfu/50µL / mice | 9 | 13 | 20 | 27 | 34 | 41 | 49 | 56 | 63 | 70 | 77 |
|---|---|---|---|---|---|---|---|---|---|---|---|---|
| IMV/EEV | 5,0 E+05 pfu | 0 | 0 | 0 | 10 | 20 | 30 | 30 | 35 | 35 | 35 | 35 |
| IMV | 5,0 E+05 pfu | 0 | 0 | 0 | 0 | 0 | 5 | 5 | 10 | 10 | 10 | 10 |
| N33 | 5,0 E+05 pfu | 0 | 0 | 0 | 0 | 0 | 0 | 0 | 0 | 0 | 0 | 0 | days after tumoral challenge

Figure 3 mice survival rates

| Groupe | VIRUS | DOSE pfu/50µL / souris | days after tumoral challenge ||||||||
|---|---|---|---|---|---|---|---|---|---|---|
| | | | 9 | 15 | 20 | 23 | 27 | 30 | 38 |
| 1 | IMV | 1,0 E+04 | 100 | 100 | 100 | 95 | 75 | 60 | 55 |
| 2 | IMV | 3,0 E+04 | 100 | 100 | 100 | 100 | 90 | 60 | 55 |
| 3 | IMV/EEV | 1,0 E+04 | 100 | 100 | 100 | 95 | 85 | 75 | 70 |
| 4 | IMV/EEV | 3,0 E+04 | 100 | 100 | 100 | 100 | 100 | 80 | 75 |
| 5 | Empty IMV | 1,0 E+04 | 100 | 100 | 100 | 60 | 30 | 10 | 5 |

PROCESS FOR PRODUCING POXVIRUSES AND POXVIRUS COMPOSITIONS

CROSS-REFERENCE TO PRIORITY/PCT APPLICATIONS

This application claims priority under 35 U.S.C. §119 of EP 06360027.4, filed Jun. 20, 2006 and Provisional Application No. 60/861,452, filed Nov. 29, 2006, and is a National Phase of PCT/EP 2007/005302, filed Jun. 15, 2007 and designating the United States (published in the English language on Dec. 27, 2007, as WO 2007/147528 A1), each hereby expressly incorporated by reference in its entirety and each assigned to the assignee hereof.

The present invention relates to compositions and pharmaceutical compositions comprising poxviruses and more particularly extracellular enveloped viruses. The present invention also relates to a process for producing poxviruses and poxviruses obtained thereof. Moreover, the present invention also relates to the use of said poxvirus and said composition for the preparation of a medicament.

The arising of new threats (avian flu, west nile virus, anthrax, etc. . . . ) as well as the development of gene therapy has increased the need for producing and purifying poxviruses for prophylactic or therapeutic purposes. This is notably the case for the Mammalian Virus Ankara (MVA). This poxvirus which was initially used for vaccinating immunodeficient patients against Variola, is now also used as a vector for gene therapy purposes. For example, MVA is utilized as a vector for the MUC1 gene for vaccinating patients against tumor expressing Muc1 (Scholl et al., 2003, J Biomed Biotechnol., 2003, 3, 194-201). MVA carrying the gene coding HPV antigens is also used as a vector for the therapeutic treatment of ovarian carcinoma.

Poxviruses are a group of complex enveloped viruses that distinguish them principally by their unusual morphology, their large DNA genome and their cytoplasmic site of replication. The genome of several members of poxviridae, including the Copenhagen vaccinia virus (VV) strain (Goebel et al., 1990, Virol. 179, 247-266 and 517-563; Johnson et al., 1993, Virol. 196, 381-401) and the modified vaccinia virus Ankara (MVA) strain (Antoine et al., 1998, Virol. 244, 365-396), have been mapped and sequenced. VV has a double-stranded DNA genome of about 192 kb coding for about 200 proteins of which approximately 100 are involved in virus assembly. MVA is a highly attenuated vaccinia virus strain generated by more than 500 serial passages of the Ankara strain of vaccinia virus on chicken embryo fibroblasts (Mayr et al., 1975, Infection 3, 6-16). The MVA virus was deposited before Collection Nationale de Cultures de Microorganismes (CNCM) under depositary $N^{602}$ I-721. Determination of the complete sequence of the MVA genome and comparison with the Copenhagen VV genome allows the precise identification of the alterations which occurred in the viral genome and the definition of seven deletions (I to VII) and numerous mutations leading to fragmented ORFs (Open Reading Frame) (Antoine et al., 1998, Virology 244, 365-396).

The natural pathway for intracellular uptake of enveloped viruses involves a series of steps including the binding of a viral polypeptide exposed at the virus surface to a cellular receptor and a fusion mechanism between the viral and cellular membranes resulting in viral genome release into the cytoplasm of the infected cell.

However, in poxvirus special case, the exact delivery pathway analysis is complicated by the existence of two morphologically distinct forms of infectious virus, termed intracellular mature virus (IMV) and extracellular enveloped virus (EEV). The IMV form is, among other particularities, characterized by a monolipid envelope surrounding the viral core and is principally localized in the cytoplasm of the infected cells, although it might be extracellularly released after lysis of the infected cells. Many of the natural polypeptides exposed at the surface of the IMV lipid envelope have been identified, such as for example the p14 kDa and p21 kDa proteins, respectively encoded by the A27L gene (Rodriguez et al., 1985, J. Virol. 56, 482-488; Rodriguez et Estaban, 1987, J. Virol. 61, 3550-3554) and the A17L gene, as well as proteins encoded by L1R, A14L, D8L, A9L (Yeh et al., 2000, J. Virol. 74, 9701-9711), E10R (Senkevich et al., 2000, Virol. 5, 244-252) and H3L genes. Compared to the IMV, the EEV form has an additional outer lipid membrane envelope (double lipid layer) acquired from the trans-Golgi network cisternae. It corresponds to the viral form released outside the infected cells. The EEV surface membrane envelope shows about 10 proteins which are absent from the IMV surface, such as for example the encoded B5R, A34R and hemagglutinin (HA) gene products. The co-existence of said IMV and EEV forms has been described for most of the vaccinia strains (e.g. Copenhagen and MVA strains) as well as for other poxviruses such as the fowl poxvirus (Boulanger et al., 2000, J. Gen. Virol. 81, 675-687).

As they are most stable in the environment, IMVs play a predominant role in a host to host transmission (Hooper et al. Virology, 2003, 306, 181-185). With this respect, IMV particles have been the vectors of choice for gene therapy purposes. For this reason, the available poxvirus purification processes only treat the virus present in the packaging cells (i.e. IMV), whereas the EEV particles shed into the culture media are discarded. Because of the presence at its surface of a larger variety of polypeptides than onto the IMV surface, the use of recombinant EEVs having a targeted infection specificity has already been proposed (US20050208074; Galmiche et al. J. Gen. Virol., 1997, 78, 3019-3027). However, even for this specific use, IMV particles are particularly preferred (US20050208074, page 4, chapter 29).

Surprisingly, the applicant has found that EEVs with no targeted infection specificity have a greater therapeutic and/or prophylactic efficacy compare to IMV.

With this respect, the present invention relates to a poxvirus and preferably a recombinant poxvirus, wherein said poxvirus is an EEV with no targeted infection specificity. The present invention also relates to a composition and preferably a pharmaceutical composition comprising recombinant EEV with no targeted infection specificity.

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

Poxvirus family comprises viruses of the Chordopoxvirus and Entomopoxvirus subfamilies. Among these, the poxvirus according to the invention is preferably chosen from the group comprising Orthopoxviruses, Parapoxviruses, Avipoxviruses, Capripoxviruses, Leporipoxviruses, Suipoxviruses, Molluscipoxviruses, Yatapoxviruses. According to a more preferred embodiment, the poxvirus of the invention is an orthopoxvirus.

The Orthopoxvirus is preferably a vaccinia virus and more preferably a modified vaccinia virus Ankara (MVA) in particular MVA 575 (ECACC V00120707) and MVA-BN (ECACC V00083008).

As previously indicated, an IMV particle comprises the viral core including the viral genome surrounded by a monolayer lipid envelope. The term "EEV" refers to an IMV particle surrounded by an additional bilayer lipid envelope exposing at its surface cellular as well as viral polypeptides.

The term "targeted infection specificity" as used herein refers to a controlled infection specificity, where a poxviral particle is engineered to display a new or enhanced tropism towards a target cell, compared to a related non modified poxvirus particle. As a result, a poxviral particle with a targeted infection specificity shows a propensity to infect said target cells unlike its related non modified poxviral particle, which means that the poxviral particle with a targeted infection specificity infects more efficiently or more rapidly its target cells (displaying at their surface the anti-ligand recognized by the ligand moiety displayed at the surface of the poxviral particle of the invention) than non target cells (that do not display at their surface such an anti-ligand), whereas a related poxviral particle with no targeted infection specificity will infect said target cells with a lower or a similar efficiency compared to non-target cells.

The term "recombinant virus" refers to a virus comprising an exogenous sequence inserted in its genome. As used herein, an exogenous sequence refers to a nucleic acid which is not naturally present in the parent virus.

In one embodiment, the exogenous sequence encodes a molecule having a directly or indirectly cytotoxic function. By "directly or indirectly" cytotoxic, we mean that the molecule encoded by the exogenous sequence may itself be toxic (for example ricin, tumour necrosis factor, interleukin-2, interferon-gamma, ribonuclease, deoxyribonuclease, *Pseudomonas* exotoxin A) or it may be metabolised to form a toxic product, or it may act on something else to form a toxic product. The sequence of ricin cDNA is disclosed in Lamb et al (Eur. J. Biochem., 1985, 148, 265-270) incorporated herein by reference.

In a preferred embodiment of the invention, the exogenous sequence is a suicide gene. A suicide gene encodes a protein able to convert a relatively non-toxic prodrug to a toxic drug. For example, the enzyme cytosine deaminase converts 5-fluorocytosine (5FC) to 5-fluorouracil (5FU) (Mullen et al (1922) PNAS 89, 33); the herpes simplex enzyme thymidine kinase sensitises cells to treatment with the antiviral agent ganciclovir (GCV) or aciclovir (Moolten (1986) Cancer Res. 46, 5276; Ezzedine et al (1991) New Biol 3, 608). The cytosine deaminase of any organism, for example *E. coli* or *Saccharomyces cerevisiae*, may be used.

Thus, in a more preferred embodiment of the invention, the gene encodes a protein having a cytosine deaminase activity and even more preferably a protein as described in patent applications WO2005007857 and WO9954481.

Other examples of pro-drug/enzyme combinations include those disclosed by Bagshawe et al (WO88/07378), namely various alkylating agents and the *Pseudomonas* spp. CPG2 enzyme, and those disclosed by Epenetos & Rowlinson-Busza (WO 91/11201), namely cyanogenic pro-drugs (for example amygdalin) and plant-derived beta-glucosidases.

Enzymes that are useful in this embodiment of the invention include, but are not limited to, alkaline phosphatase useful for converting phosphate-containing prodrugs into free drugs; arylsulfatase useful for converting sulfate-containing prodrugs into free drugs; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as beta-galactosidase and neuraminidase useful for converting glycosylated prodrugs into free drugs; beta-lactamase useful for converting drugs derivatized with beta-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as abzymes, can be used to convert the prodrugs of the invention into free active drugs (Massey R. et al., Nature, 1987, 328, 457-458).

Similarly, prodrugs include, but are not limited to, the above-listed prodrugs, e.g., phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted. Examples of cytotoxic drugs that can be derivatized into a prodrug form for use in this invention include, but are not limited to, etoposide, teniposide, adriamycin, daunomycin, carminomycin, aminopterin, dactinomycin, mitomycins, cis-platinum and cis-platinum analogues, bleomycins, esperamicins (see for example U.S. Pat. No. 4,675,187), 5-fluorouracil, melphalan and other related nitrogen mustards.

In a further embodiment the exogenous gene encodes a ribozyme capable of cleaving targeted RNA or DNA. The targeted RNA or DNA to be cleaved may be RNA or DNA which is essential to the function of the cell and cleavage thereof results in cell death or the RNA or DNA to be cleaved may be RNA or DNA which encodes an undesirable protein, for example an oncogene product, and cleavage of this RNA or DNA may prevent the cell from becoming cancerous.

In a still further embodiment the exogenous gene encodes an antisense RNA.

By "antisense RNA" we mean an RNA molecule which hybridises to, and interferes with the expression from a mRNA molecule encoding a protein or to another RNA molecule within the cell such as pre-mRNA or tRNA or rRNA, or hybridises to, and interferes with the expression from a gene.

In another embodiment of the invention, the exogenous sequence replaces the function of a defective gene in the target cell. There are several thousand inherited genetic diseases of mammals, including humans, which are caused by defective genes. Examples of such genetic diseases include cystic fibrosis, where there is known to be a mutation in the CFTR gene; Duchenne muscular dystrophy, where there is known to be a mutation in the dystrophin gene; sickle cell disease, where there is known to be a mutation in the HbA gene. Many types of cancer are caused by defective genes, especially protooncogenes, and tumour-suppressor genes that have undergone mutation.

Examples of protooncogenes are ras, src, bcl and so on; examples of tumour-suppressor genes are p53 and Rb.

In a further embodiment of the invention, the exogenous sequence encodes a Tumor Associated Antigen (TAA). TAA refers to a molecule that is detected at a higher frequency or density in tumor cells than in non-tumor cells of the same tissue type. Examples of TAA includes but are not limited to CEA, MART-1, MAGE-1, MAGE-3, GP-100, MUC-1, MUC-2, pointed mutated ras oncogene, normal or point mutated p53, overexpressed p53, CA-125, PSA, C-erb/B2, BRCA I, BRGA II, PSMA, tyrosinase, TRP-1, TRP-2, NY-ESO-1, TAG72, KSA, HER-2/neu, bcr-abl, pax3-fkhr, ews-fli-1, surviving and LRP. According to a more preferred embodiment the TAA is MUC1.

The recombinant poxvirus can comprise more than one exogenous sequence and each exogenous sequence can encodes more than one molecule. For example, it can be useful to associate in a same recombinant poxvirus, an exogenous sequenced coding a TAA with an exogenous sequence coding a cytokine.

In another embodiment of the invention, the exogenous gene encodes an antigen. As used herein, "antigen" refers to a ligand that can be bound by an antibody; an antigen need not itself be immunogenic.

Preferably the antigen is derived from a virus such as for example HIV-1, (such as gp 120 or gp 160), any of Feline Immunodeficiency virus, human or animal herpes viruses, such as gD or derivatives thereof or Immediate Early protein such as ICP27 from HSV1 or HSV2, cytomegalovirus (such as gB or derivatives thereof), Varicella Zoster Virus (such as gpI, II or III), or from a hepatitis virus such as hepatitis B virus for example Hepatitis B Surface antigen or a derivative thereof, hepatitis A virus, hepatitis C virus (preferentially non structural protein from genotype 1b strain ja) and hepatitis E virus, or from other viral pathogens, such as Respiratory Syncytial Virus, Human Papilloma Virus (preferentially the E6 and E7 protein from the HPV16 strain) or Influenza virus, or derived from bacterial pathogens such as *Salmonella, Neisseria, Borrelia* (for example OspA or OspB or derivatives thereof), or *Chlamydia*, or *Bordetella* for example P.69, PT and FHA, or derived from parasites such as *plasmodium* or *Toxoplasma*.

In a particularly preferred embodiment of the invention, the recombinant poxvirus encodes the same proteins than TG4010 (Rochlitz et al. J Gene Med. 2003 August; 5(8):690-9) and TG4001 (Liu et al. Proc Natl Acad Sci USA. 2004 Oct. 5; 101 Suppl 2:14567-71). In another particularly preferred embodiment of the invention, the poxvirus of the invention has a sequence which is more than 90% homologous to the sequence of TG4010 or of TG4001.

Advantageously, the recombinant poxvirus further comprises the elements necessary for the expression of the exogenous sequence. The elements necessary for the expression comprise of the set of elements allowing the transcription of a nucleotide sequence to RNA and the translation of a mRNA to a polypeptide, in particular the promoter sequences and/or regulatory sequences which are effective in the cell to be infected by the recombinant poxvirus of the invention, and optionally the sequences required to allow the excretion or the expression at the surface of the cells for said polypeptide. These elements may be inducible or constitutive. Of course, the promoter is adapted to the recombinant poxvirus selected and to the host cell. There may be mentioned, by way of example, the vaccinia virus promoters p7.5K pH5R, pK1L, p28, p11 or a combination of said promoters. The literature provides a large amount of information relating to such promoter sequences.

The elements necessary may, in addition, include additional elements which improve the expression of the exogenous sequence or its maintenance in the host cell. There may be mentioned in particular the intron sequences (WO 94/29471), secretion signal sequences, nuclear localization sequences, internal sites for reinitiation of translation of the IRES type, poly A sequences for termination of transcription.

Available poxvirus production processes comprised the replication of the virus in a cell line (e.g. HelaS3), in embryonated eggs or in Chicken Embryo Fibroblasts. After the replication of the virus, the culture media is discard, the cells are lysed and the poxvirus released from the cells is purified by sucrose cushion centrifugation (Kotwal and Abraham; Poxvirus growth, Purification and tittering in Vaccinia Virus and Poxvirology, 2004, 101-108, Humana Press Inc., Totowa; NJ; USA). With these processes, no EEVs are present in the purified composition.

However, the available virus production processes are not satisfactory. Firstly, they comprise the use of compounds deriving from animals such as serum and enzymes. The use of compounds deriving from animals in production processes has several drawbacks. For example, the chemical composition of these compounds may vary between lots, even from a single manufacturer. The compounds may also be contaminated with infectious agents (e.g., mycoplasma and viruses) which can seriously undermine the health of the cultured cells when these contaminated supplements are used in cell culture media formulations. Moreover, the use of serum supplementation of culture media can complicate and increase the costs of the purification of the desired substances from the culture media due to nonspecific co-purification of serum or extract proteins. Most importantly, the use of undefined compounds may hinder the approval by medical agencies of the pharmaceutical composition obtained by the process.

The present invention further provides a process for producing a poxviral particle according to the invention, comprising the steps of:

a) preparing a culture of packaging cells,
b) infecting said cell culture,
c) culturing said infected cells for an appropriate period of time,
d) recovering the poxviral particles produced from the culture supernatant and/or the packaging cells, and
e) optionally, purifying the recovered poxviral particles.

The process according to the invention is preferably free from animal products.

The process according to the invention can also be used for the production of a wild type, and/or an attenuated poxvirus.

As used herein, the term "attenuated poxvirus" refers to any poxvirus that has been modified so that its pathogenicity in the intended subject is substantially reduced. Preferably, the poxvirus is attenuated to the point it is nonpathogenic from a clinical standpoint, i.e., that subjects exposed to the poxvirus do not exhibit a statistically significant increased level of pathology relative to control subjects. According to a preferred embodiment of the invention, the attenuated virus is an attenuated Vaccinia virus such as MVA.

The term "infection" refers to the transfer of the viral nucleic acid to a cell, wherein the viral nucleic acid is replicated, viral proteins are synthesized, or new viral particles assembled.

As used herein, the term "packaging cell" refers to a cell which can be infected by the poxvirus to be produced. The packaging cell can be a primary cell, a recombinant cell and/or a cell line. For example, a recombinant cell which contains the elements necessary for the production of a recombinant virus which are lacking in a recombinant viral vector can be used.

In one embodiment of the invention, the packaging cell is an immortal avian cell.

In one embodiment of the invention, the packaging cell is a DF1 cell (U.S. Pat. No. 5,879,924), which is a spontaneously immortalized chicken cell line derived from 10 day old East Lansing Line (ELL-0) eggs.

Immortal avian cell can be derived from embryonic stem cells by progressive severance from growth factors and feeder layer, thus maintaining growth features and infinite lifespan characteristic of undifferentiated stem). For example, the Ebx chicken cell line (WO2005007840) has been obtained by this process.

According to a preferred embodiment, a duck embryo permanent cell line can also be used. For example, the cell line, designated as DEC 99 (Ivanov et al. Experimental Pathology And Parasitology, 4/2000 Bulgarian Academy of Sciences) has been cultured over 140 consecutive passages and it is not tumorogenic for birds. The DEC 99 cell line is a standard cell culture system that has been used for research and can be applied for the needs of biotechnology. According to a more preferred embodiment, the packaging cell is a cell line obtained by the process disclosed in patent application EP06360001.9.

According to another preferred embodiment, the packaging cell used in the process according to the invention is a chicken embryo fibroblast (CEF). The preparation and use of CEF for the production of viruses are well known to the one skilled in the art.

CEF are preferably extracted from Specific Pathogen Free (SPF) eggs. SPF eggs are commercially available, for example from Charles River Laboratories (Wilmington, Mass., USA). Said eggs are preferably more than 9 days old, more preferably between, 10 and 14 days old and even more preferably are 12 days old.

Before the extraction of the embryo, the egg is preferably disinfected. Many methods and products dedicated to the disinfection of eggs are available in the prior art. Incubation in a formol solution (e.g. 2% formol, 1 min.) followed by a rinsing in 70% ethanol is particularly preferred.

The cells of the embryos are then dissociated and purified. According to a preferred embodiment of the invention, the cells are subjected to an enzymatic digestion step that allows the destruction of the intercellular matrix. For this purpose, the use of enzyme able to digest the intercellular matrix is particularly useful. Such enzyme can be selected from the group comprising but not limited to Trypsin, Collagenase, Pronase, Dispase, Hyaluronidase and Neuraminidase. This enzyme can be used alone or in combination. In a particularly preferred embodiment of the invention dispase and Tryspsin (e.g. TrypLE select from Gibco™) are used in combination. The one skilled in the art is able to determine the enzyme concentration, the temperature and the length of incubation allowing an efficient separation of the cells.

According to a preferred embodiment, the process according to the invention is free from animal products (except the packaging cell). With this respect, the enzyme(s) used for the preparation of CEF is (are) preferably of recombinant origin. As used herein, <<animal products>> means any compound or collection of compounds that was produced in or by an animal cell in a living organism.

The preparation of CEF can further includes a filtration step (and/or a centrifugation step in order to remove contaminants.

This primary CEF cell can either be used directly or after one further cell passage as secondary CEF cell.

The one skilled in the art is able to select the most appropriate cell for the production of a specific virus. According to a preferred embodiment, the process according to the invention comprises the use of CEF or a cell according to EP06360001.9 for the production of a MVA.

The packaging cell used in the process according to the invention is cultivated in an appropriate cell culture media. It is possible to use more than one culture medium in the process according to the invention. For example, a first culture medium can be used during the preparation of the packaging cell (i.e. during step a) and a second cell culture medium for the infection (i.e. during step c and/or step b).

According to a preferred embodiment, the cell culture media according to the invention is free from animal product.

Many media free from animal product has been already described and some of them are commercially available. For example 293 SFM II; 293-F Cells, SFM Adapted; 293-H Cells, SFM Adapted; 293Fectin™ Transfection Reagent; CD 293 AGT™; CD 293 Medium; FreeStyle™ 293 Expression System; FreeStyle™ 293 Medium; FreeStyle™ 293-F Cells, SFM Adapted; Adenovirus Expression Medium (AEM) Growth Medium for PER.C6® Cells; CD 293 AGT™; CD 293 Medium; COS-7L Cells, SFM Adapted; EPISERF® Medium; OptiPro™ SFM; VP-SFM; VP-SFM AGT™. (all available from invitrogen) can be used as cell culture media in the process according to the invention.

When the packaging cell is a CEF, VP-SFM (invitrogen) for step a and Basal Medium Eagle (invitrogen) for step b and c are particularly preferred.

In the specific embodiment where the packaging cells are CEF, the cell culture medium is seeded with between 0.5 to 1.5 and preferably between 1.1 and 1.3 and more preferably about 1.2 embryo/l of cell culture medium. In this embodiment, the CEF are preferably cultivated for between 1 and 5 days, more preferably between 1 and 2 days and even more preferably 2 days before infection.

In the specific embodiment where the poxvirus to produce is MVA, the virus is introduced in the cell culture vessel at a MOI which is preferably comprised between 0.001 and 0.1, more preferably between 0.03 and 0.07 and even more preferably about 0.05.

According to a preferred embodiment of the invention, during step c, the packaging cells are cultivated at a temperature which is lower than 37° C., preferably between 30° C. and 36.5° C. or between about 32° C. and about 36° C., more preferably between 33° C. and 35° C., most preferably at 34° C.

According to preferred embodiment of the invention, step c lasts between one and six days, more preferably between two and four days and most preferably about 72 hours.

After the infection step, the cell culture media used to cultivate the packaging cell is collected. Said cell culture media comprised the EEV particles shed by the infected packaging cell. According to a preferred embodiment, after the infection step, the cell culture media and the packaging cell are collected. The cell culture media and the packaging cells can be pooled or collected separately.

In order to recover the poxviruses present in the packaging cells, the process according to the invention may comprises a step allowing the disruption of the packaging cell membrane. This step leads to the liberation of the poxvirus from the packaging cell. The disruption of the packaging cell membrane can be induced by various techniques well known by the one skilled in the art. These techniques comprised but are not limited to sonication, freeze/thaw, hypotonic lysis and microfluidization.

According to a preferred embodiment of the invention, the packaging cell membrane is disrupted by using a high speed homogenizer. High speed homogenizers are commercially available from Silverson Machines Inc (East Longmeadow, USA) or Ika-Labotechnik (Staufen, Germany). According to particularly preferred embodiment, said High Speed homogeneizer is a SILVERSON L4R.

When the packaging cell and the cell culture media are pooled, the disruption of the packaging cell membrane is not induced by freeze/thaw as this technique leads to the destruction of the EEV particles (Ichihashi y. et al., 1996, virology, 217(2), 478-85).

According to a preferred embodiment, step d) further comprises a clarification step allowing the withdrawal of the cellular debris. According to a more preferred embodiment of the invention, said clarification step is a depth filtration step.

Depth filtration includes but are not limited to the use of one or more commercially available products: CUNO Incorporated AP series depth filters (Examples include AP01), CUNO Incorporated CP series depth filters (Example include CP10, CP30, CP50, CP60, CP70, CP90), CUNO Incorporated HP series depth filters Examples include HP10, HP30, HP50, HP60, HP70, HP90), CUNO Incorporated Calif. series depth filters (Examples include CA10, CA30, CA50, CA60, CA70, CA90), CUNO Incorporated SP series depth filters (Examples include SP10, SP30, SP50, SP60, SP70, SP90), CUNO Delipid and Delipid Plus filters, Millipore Corporation CE series depth filters (Examples include CE15, CE20, CE25, CE30, CE35, CE40, CE45, CE50, CE70, CE75), Millipore Corporation DE series depth filters (Examples include DE25, DE30, DE35, DE40, DE45, DE50, DE55, DE560, DE65, DE70, DE75), Millipore Corporation HC filters (Examples include A1HC, B1HC, COHC), CUNO Polynet Filters (An example include Polynet-PB), Millipore Clarigard and Polygard filters, CUNO Life Assure filters, ManCel Associates depth filters (Examples include but are not limited to PR 12 UP, PR12, PR 5 UP), and PALL or SeitzSchenk Incorporated filters. In order to improve the clarification capacity of the available depth filtration units, it can be useful to couple two or more units with decreasing pore sizes. In this embodiment, the mixture to be clarified passes through the first depth filtration unit where the biggest contaminants are retained and subsequently passes through the second depth filtration unit. According to an even more preferred embodiment of the invention, a sartopure© (sartorius) with a pore size of 8 µm coupled to a sartopure© with a pore size of 5 µm is used for the depth filtration step.

According to a preferred embodiment, the process according to the invention further comprises a concentration step. More preferably, said concentration step further allows the elimination of the proteins present in the mixture obtained from the previously described steps.

According to a more preferred embodiment of the invention, said concentration step is a microfiltration step. Microfiltration is a pressure driven membrane process that concentrates and purifies large molecules. More specifically, a solution is passed through a semi-permeable membrane whose pore sizes have been chosen to reject the large particles (viruses) in the retentate, and allow the small molecules (e.g. proteins) to pass through the membrane into the permeate. Microfiltration reduces the volume of the extraction solution.

According to a preferred embodiment of the invention, the microfiltration step is followed by a diafiltration step. These two steps can advantageously be done with the same filtration membranes. Diafiltration is an improvement of microfiltration and involves diluting the retentate with a solution to effect a reduction in the concentration of the impurities in the retentate. The dilution of the retentate allows washing out more of the impurities from the retentate. It is understood that the diafiltration may be carried out in a batch mode, semi-continuous mode, or a continuous mode. The diafiltration step can be advantageously used to change the buffer in which the virus is comprised. For example, it can be useful to exchange the buffer used in the purification process against a pharmaceutically acceptable buffer Preferably, the filtration membranes used in the microfiltration and/or in the diafiltration step have a pore size comprised between 0.01 and 0.15 μm, and more preferably about 0.1 μm.

Nucleic acids may adhere to cell derived particles such as viruses. With this respect, the process according to the invention can optionally further comprises a step consisting in removing the contaminating nucleic acids present in the solution. For this purpose, nucleases can be utilized. Exemplary nucleases include Benzonase or any other DNase or RNase commonly used within the art, among them, Benzonase is particularly preferred.

Benzonaze degrades nucleic acid and have no proteolytic activity. Benzonase rapidly disintegrates nucleic acid by hydrolyzing internal phosphodiester bonds between specific nucleotides. Upon complete digestion, all free nucleic acids present in solution are reduced to oligonucleotides 2 to 4 bases in length.

Benzonase can be used at a final concentration comprised between 50 and 400 U/ml, preferably between 100 and 300 U/ml and more preferably between 150 and 250 U/ml. The Benzonase treatment can last between 1 and 4 hours and even more preferably between 1.5 and 2.5 hours.

However, when the depth filtration, microfiltration and diafiltration previously described are used, the use of nucleases and more particularly, the use of benzonase is not necessary. With this respect, the present invention also relates to a process for the production of poxviruses wherein no nuclease and more particularly no benzonase is used.

At this stage, the poxvirus obtained by the process previously described is sufficiently purified. It can be desirable to change the buffer in which the virus is comprised. For example, it can be useful to exchange the buffer used in the purification process against a pharmaceutically acceptable buffer. Many methods usable to change the buffer are known to the one skilled in the art. Among them, tangential filtration is particularly preferred.

Tangential filtration is a filtration technique wherein the suspension to be filtered moves at a high speed along a direction which is parallel to filtrating surface in order to create a suspension turbulence which prevents the filtration cake formation as well as the frequent filter blocking.

While suspension flows at high speed parallel to filtering surface, solute passes through the filtering surface holes because of the pressure difference and is continuously removed. Filtering surface should be such as to mechanically resist to pressure difference between the retentate compartment (i.e. the suspension concentrating compartment) and the permeate compartment (clear filtered solution free from suspended particles).

The various steps comprised in the process according to the invention can be implemented in separated working places and/or in different time periods. For example, the infection of the packaging cell and the purification of the poxviruses can be made in different working places. As well, the packaging cell and/or the cell culture media can be stored (e.g at −80° C.) as long as necessary, before being purified.

The present invention also relates to compositions obtained by the process previously described and to composition comprising the poxvirus of the invention.

Preferably, the composition of the invention comprises more than 1%, preferably more than 5%, even more preferably more than 10% and most preferably at least 20% of the poxviruses comprised in said composition are EEV.

According to a preferred embodiment, the composition according to the invention has a titer of at least $10^5$, preferably of at least $10^6$, more preferably of at least $10^7$, even more preferably of at least $10^8$ pfu per ml.

According to another preferred embodiment, the composition according to the invention has a titer of at least $10^3$, preferably $10^4$ and most preferably at least 3 $10^5$ pfu per μg of protein.

The present invention also relates to pharmaceutical composition comprising the poxvirus obtained by the process of the invention, and/or composition according to the invention. As used herein, "pharmaceutical composition" refers to a composition comprising a pharmaceutically acceptable carrier.

Such a carrier is preferably isotonic, hypotonic or weakly hypertonic and has a relatively low ionic strength, such as for example a sucrose solution. Moreover, such a carrier may contain any solvent, or aqueous or partially aqueous liquid such as nonpyrogenic sterile water. The pH of the pharmaceutical composition is, in addition, adjusted and buffered so as to meet the requirements of use in vivo. The pharmaceutical composition may also include a pharmaceutically acceptable diluent, adjuvant or excipient, as well as solubilizing, stabilizing and preserving agents. For injectable administration, a formulation in aqueous, nonaqueous or isotonic solution is preferred. It may be provided in a single dose or in a multidose in liquid or dry (powder, lyophilisate and the like) form which can be reconstituted at the time of use with an appropriate diluent.

The present invention also relates to the poxvirus and the composition obtained by the process according to the invention.

The present invention also relates to the use of a process according to the invention for the production of a virus, a composition and/or a pharmaceutical composition.

The present invention also relates to the use of a poxvirus, a composition and/or a pharmaceutical composition according to the invention for the preparation of a medicament.

According to a preferred embodiment the medicament according to the invention is for the therapeutic or prophylactic treatment of cancer.

Among the applications which may be envisaged, there may be mentioned cancers of the breast, of the uterus (in particular those induced by papilloma viruses), of the prostate, of the lungs, of the bladder, of the liver, of the colon, of the pancreas, of the stomach, of the esophagus, of the larynx, of the central nervous system (in particular glyoma) and of the blood (lymphomas, leukemia and the like).

A composition according to the invention may be manufactured conventionally for administration by the local, parenteral or digestive route. The routes of administration which may be envisaged are many. There may be mentioned, for example, the intragastric, subcutaneous, intracardiac, intramuscular, intravenous, intraperitoneal, intratumor, intranasal, intrapulmonary or intratracheal route. For the latter three embodiments, administration by aerosol or instillation is advantageous. The administration may be made as a single dose or repeated once or several times after a certain time interval. The appropriate route of administration and dosage vary as a function of various parameters, for example, of the individual, of the disease to be treated or of the gene(s) of interest to be transferred.

According to a first possibility, the medicament may be administered directly in vivo (for example by intravenous injection, into an accessible tumor or at its periphery, subcutaneously for a therapeutic or prophylactic vaccination). It is also possible to adopt the ex vivo approach which consists in collecting cells from the patient (bone marrow stem cells, peripheral blood lymphocytes, muscle cells and the like), transfecting or infecting them in vitro according to prior art techniques and readministering them to the patient.

It is moreover possible to envisage, where appropriate and without departing from the scope of the present invention, carrying out simultaneous or successive administrations, by different routes, of the various components contained in the pharmaceutical composition or composition according to the invention.

According to an advantageous embodiment of the invention, the therapeutic use or the method of treatment is combined with a second treatment of the patient by surgery (partial or complete removal of the tumor), by radiotherapy or chemotherapy. In this particular case, the treatment according to the invention is applied prior to, concomitantly with or subsequent to said second treatment. Preferably, this treatment will be applied subsequent to said second treatment.

According to another preferred embodiment the medicament according to the invention is for the therapeutic or prophylactic treatment of infectious diseases, in particular of viral origin, induced by hepatitis B or C viruses, HIV, herpes, retroviruses and the like

BRIEF DESCRIPTION OF DRAWINGS

The examples which follow are intended to illustrate the various subjects of the present invention and are consequently not limiting in character.

Table 1: depicts the survival rate of C57BL/6 mice which as been implanted with TC1 cells expressing HPV 16 E6 and E7 and C-Ha-ras oncogene. The different groups of mice are treated with compositions comprising IMV and EEV encoding HPV antigens, IMV encoding the HPV antigens or IMV encoding no antigens.

Table 2: depicts percentage of C57BL/6 mice free from tumor after implantation with TC1 cells expressing HPV 16 E6 and E7 and C-Ha-ras oncogene. The different groups of mice are treated with compositions comprising IMV and EEV encoding HPV antigens, IMV encoding the HPV antigens or IMV expressing no antigens.

Table 3: depicts the survival rate of C57BL/6 mice which as been implanted with TC1 cells expressing MUC1. The different groups of mice are treated with compositions comprising IMV and EEV encoding MUC1 and IL2, IMV encoding MUC1 and IL2 or IMV expressing no antigens.

EXAMPLES

1. Preparation of Compositions Comprising IMV and EEV

A. Preparation of CEF.

Sixty six SPF eggs are incubated in for 60s. in a 2% formol solution. After being rinsed with 70% ethanol, the eggs are open, the embryos are extracted and dissected. The obtained tissues are then digested at 36.5° C. for 120 min by dispase (Ul/ml) and triple select (Ul/ml).

The mixture is filtrated to remove undigested tissues and the CEF are collected by centrifugation (2300 rpm, 15 min.)

B. CEF Cultivation and Infection.

The CEF are incubated in 55 l of VP-SFM (invitrogen) for 2 days at 36.5° C. The cell culture media is then discarded and the poxvirus (0.05 MOI) is added in 55 l of Basal Medium Eagle (invitrogen). The infected packaging cells are then incubated for three days.

C. Poxvirus Purification.

The packaging cell and the cell culture media are collected. The mixture is then homogenised for 15 min. with a Silverson© L4R high speed homogeniser. The obtained mixture is then clarified by depth filtration on a sartopure 8 μm (sartorius) coupled to a sartopure 5 μm at a flow rate of 1 l/min.

The mixture is further concentrated 18 times through a 0.1 μm Prostak Microfiltration Module (ref: PSVVAG021, Millipore).

The poxviral composition is further diafiltrated on the same module against the desired pharmaceutically acceptable carrier.

2. Therapeutic Efficiency Comparison Between a Composition Comprising EEV and IMV and a Composition Comprising IMV Only A. Therapeutic Treatment of Mice Bearing Tumor Expressing HPV Antigens.

Denomination and Brief Description of Each Vector Construction

TG4001: MVA vector carrying the coding sequences for HPV proteins, E6 and E7, (under the control of promoter p7.5) and IL2 (under the control of promoter pH5R). Two lots, one comprising IMV and EEV (prepared as previously disclosed) and one comprising only IMV were tested.

N33: empty vector MVA which expresses neither HPV proteins E6 and E7 nor IL2 was used as negative control.

Animal Model

C57Bl/6 female mice aged 6 to 8 weeks were used throughout this study. These mice were obtained from Charles River (Rouen, France).

Specification: The animals were 6 week old on the arrival day. At the beginning of experimentation, they were less than 8 week old.

Environment: The animals were housed in a single, exclusive room air-conditioned to provide a minimum of 11 air changes per hour. The temperature and relative humidity ranges were within 18° C. and 22° C. and 40 to 70% respectively. Lighting was controlled automatically to give a cycle of 12 hours of light and 12 hours of darkness.

Specific pathogen free status is checked by regular control of the environment.

Diet: Throughout the study the animals had access ad libitum to sterilized diet type D04 (UAR, Epinay sur Orge, France). Water was provided ad libitum via bottles.

Acclimatization and health procedures: All animals were given a clinical inspection for health on arrival. They were acclimatized in a specific pathogen free (SPF) animal facility between one and two weeks before the start of the experiment in order to ensure their suitability for the study.

Tumor Cells Characteristics and Conditions of Use:

The TC1 line has been derived from primary lung epithelial cells of C57Bl/6 mice co-transformed with HPV-16 E6 and E7 and c-Ha-ras oncogenes. These cells grow in DMEM with Glutamine (2 mM), fetal calf serum (10%), non essential amino acids (0.1 mM), Na Pyruvate (1mM), β mercaptoethanol (36 μM), Hygromycine (0.2 mg/ml) and G418 (0.5 mg/ml). After thawing, cells were amplified two times, the latest passage was performed two days before the cell injection.

Cells Injection

The first day of the experiment, TC1 cells were injected subcutaneously in mice at a dose of 2.0 E+05 cells/mouse in the flank.

Viral Injections 7 days after the cells injection, 5.0 E+05 pfu/50 μl/mouse of tested lots (TG4001 IMV/EEV or IMV only) MVATGN33 (empty vector) were injected into mice. Twenty mice were used per tested lot.

Viral injections were performed subcutaneously in the same flank but at a distant site from the cells injection point and carried out 3 times at 7 day intervals.

Parameters of Monitoring:

Tumor growth was monitored for 90 days after the cells injection, with a caliper. Mice were sacrificed for ethical reasons when the tumor size was superior to 25 mm in diameter or when they showed pain even if the tumor was smaller.

Surviving mice were recorded.

Results

All the groups treated with the MVA vector encoding HPV antigen showed a higher survival rate than the group treated with an empty MVA vector. The mice treated with the composition comprising EEV and IMV showed a higher survival rate than the mice treated by composition comprising IMV only. Moreover, 35% of the mice treated by the composition comprising EEV and IMV were free from tumor 77 days after being injected compared to only 10% of the mice treated by the composition comprising only IMV.

B. Therapeutic Treatment of Mice Bearing Tumor Expressing MUC1.

Denomination and Brief Description of Each Vector Construction

TG4010: MVA vector carrying the coding sequences for MUC1 proteins (under the control of promoter p7.5) and IL2 (under the control of promoter pH5R). Two lots, one comprising IMV and EEV and one comprising only IMV were tested.

An empty vector MVATGN33 which expresses neither MUC1, nor IL2 was used as negative control.

Mouse Model and Animal Experiments System

Species, strain and supplier: C57Bl/6 female mice aged 6 to 8 weeks were used throughout this study. These mice were obtained from Charles River (Rouen, France).

Specification: The animals were 6-week old on the arrival day. At the beginning of experimentation, they were less than 8 week old.

Environment: The animals were housed in a single, exclusive room air-conditioned to provide a minimum of 11 air changes per hour. The temperature and relative humidity ranges were within 18° C. and 22° C. and 40 to 70% respectively. Lighting was controlled automatically to give a cycle of 12 hours of light and 12 hours of darkness.

The animals were housed in-groups of 10 per cages of 43×27×15 cm, floor area 1161 cm².

Diet: Throughout the study the animals had access ad libidum to sterilized diet type RM (SDS, Le Bord'Haut de Vigny, France).

Water was provided ad libidum via bottles.

No contaminants were present in diet or water at levels, which might have interfered with achieving the objectives of the study.

Acclimation and health procedures: All animals were given a clinical inspection for health on arrival. They were acclimatized in a Specific Pathogen Free (SPF) animal facility between one and two weeks before the start of the experiment in order to ensure their suitability for the study.

Tumor Cells Characteristics and Conditions of Use:

The RMA tumor line has been derived from a C57Bl/6 lymphoma. RMA-MUC1 cells were obtained after transfection with an expression plasmid containing the MUC1 gene a. These cells were grown in DMEM with Glutamine (2 mM), fetal calf serum (10%), non essential amino acids (0.1 mM), Na Pyruvate (1 mM), β mercapto-ethanol (36 μM) and Hygromycine (550 μg/ml). After thawing, cells were amplified two times, the latest passage was performed the day before challenge.

Immunization

Mice were immunized with 1.0 104 or 3.0 104 pfu/mouse for TG4010 virus and with 3.0 104 pfu/mouse for MVATGN33.

20 mice were used per tested lot.

Viral immunizations were performed subcutaneously in a flank and carried out 3 times at 14 day intervals.

Tumor Challenge

Two weeks after the last immunization, mice were challenged subcutaneously in the same flank but at a distant site from the viral injections point, with 1.0 E+06 RMA-MUC1 viable cells/50 μl/mouse.

Parameters of Monitoring:

Tumor growth was monitored for 6 weeks after the tumor challenge, with a caliper. Mice were sacrificed for ethical reasons when the tumor size was superior to 25 mm in diameter or when they showed pain even if the tumor was smaller.

Surviving mice were recorded.

20 mice were used per dose.

Results.

All the groups treated with the MVA vector encoding the MUC1 antigen showed a lower tumor growth and a higher survival rate than the group treated with an empty MVA vector. The mice treated with the composition comprising EEV and IMV showed a lower tumor growth than the mice treated by composition comprising only IMV.

The invention claimed is:

1. A process for producing a composition of a wild type, an attenuated, and/or a recombinant poxvirus with no targeted infection specificity comprising the steps of:
   a) preparing a cell culture of packaging cells,
   b) infecting said cell culture to obtain infected cells,
   c) culturing said infected cells for an appropriate period of time to produce poxviral particles,
   d) recovering said poxviral particles from the culture supernatant, and from packaging cells disrupted by high speed homogenizer, to obtain a poxviral particle mixture,
   e) clarifying said poxviral particle mixture, thereby removing cellular debris, wherein said clarifying comprises depth filtration, to obtain a clarified poxviral particle mixture;
   f) concentrating said clarified poxviral particle mixture, wherein said concentrating comprises microfiltration, to obtain a concentrated poxviral particle mixture, and
   g) diafiltrating said concentrated poxviral mixture,
   wherein said process is free from animal products and does not use nuclease and
   wherein said composition comprises intracellular mature virus ("IMV") and extracellular enveloped virus ("EEV") with more than 1% of EEV.

2. The process of claim 1, wherein said packaging cell is a chicken embryo fibroblast ("CEF").

3. The process of claim 1, wherein step c) lasts from two to four days.

4. The process of claim 1, wherein said composition comprises more than 5% of EEV.

5. The process of claim 1, further comprising the step of exchanging the buffer used in the purification process with a pharmaceutically acceptable buffer.

6. The process of claim 5, wherein said step is performed by tangential filtration.

* * * * *